US00PP11796P2

(12) United States Plant Patent
Bergman

(10) Patent No.: US PP11,796 P2
(45) Date of Patent: Mar. 6, 2001

(54) HIBISCUS PLANT NAMED 'WHIRL WIND'

(75) Inventor: Wendy R. Bergman, Lehigh Acres, FL (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/333,131

(22) Filed: Jun. 14, 1999

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Whirl Wind', characterized by its very glossy, undulate, very dark green leaves; upright, outwardly spreading, uniform, dense and symmetrical plant habit that is appropriate for container production; very freely flowering; numerous dark pink and pale pink bi-colored-flowers with dark red "eyes"; good resistance to flower bud abscission; and excellent postproduction longevity.

2 Drawing Sheets

BACKGROUND OF THE INVENTION

The present invention relates to a new and distinct cultivar of Hibiscus, botanically known as *Hibiscus rose-sinensis* and hereinafter referred to by the cultivar name Whirl Wind.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, resistance to flower bud abscission, and good postproduction longevity.

The new Hibiscus origninated from a cross made by the Inventor in Alva, Fla., of the *Hibiscus rosa-sinensis* cultivar Waikiki, disclosed in U.S. Plant Pat. No. 7,834, as the female, or seed, parent with the *Hibiscus rosa-sinensis* cultivar Florida Sunset, not patented, as the male, or pollen, parent. The cultivar Whirl Wind was discovered and selected by the Inventor as a flowering plant within the progeny of the stated cross in a controlled environment in Alva, Fla., on Oct. 13, 1995.

Compared to plants of the female parent, the cultivar Waikiki, plants of the new Hibiscus have smaller flowers and flower several days earlier. In addition, plants of the new Hibiscus have bi-colored flowers, that is, dark pink petals with a pale pink picotee margin, whereas plants of the cultivar Waikiki are solid pink. Plants of new Hibiscus are much more uniform in plant habit; have darker green, thicker and more attractive leaves; produces more flowers per plant per day; and differ in flower color compared to plants of the male parent, the cultivar Florida Sunset.

Asexual reproduction of the new Hibiscus by terminal cuttings taken in a controlled environment in Alva, Fla., has shown that the unique features of this new Hibiscus are stable and reproduced true to type in successive generations.

SUMMARY OF THE INVENTION

The cultivar Whirl Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Whirl Wind'. These characteristics in combination distinguish 'Whirl Wind' as a new and distinct cultivar:

1. Very glossy, undulate, very dark green leaves.
2. Upright, outwardly spreading, uniform, dense and symmetrical plant habit that is appropriate for container production.
3. Very freely flowering, numerous dark pink and pale pink bi-colored-colored flowers with dark red "eyes".
4. Good resistance to flower bud abscission.
5. Excellent postproduction longevity.

Plants of the new Hibiscus can be compared to plants of the cultivar Bimini Breeze, disclosed in U.S. Plant Pat. No. 10,582. However, in side-by-side comparisons conducted in Alva, Fla., plants of the new Hibiscus differ from plants of the cultivar Bimini Breeze in the following characteristics:

1. Plants of the new Hibiscus have lighter green leaves than plants of the cultivar Bimini Breeze.
2. Plants of the new Hibiscus flower more uniformly than plants of the cultivar Bimini Breeze.
3. Flowers of plants of the new Hibiscus are slightly smaller than flowers of plants of the cultivar Bimini Breeze.
4. Plants of the new Hibiscus and the cultivar Bimini Breeze differ in flower color as plants of the new Hibiscus are bi-colored, whereas plants of the cultivar Bimini Breeze are solid pink in color.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type.

The photograph on the first sheet comprises a side perspective view of a typical plant of 'Whirl Wind'.

The photograph on the second sheet comprises a close-up view of a typical flower of 'Whirl Wind'. Both photographs were taken when plants were about 7 months old. Flower and foliage colors in the photographs may appear different from the actual colors due to light reflectance.

DETAILED BOTANICAL DESCRIPTION

The following observations, measurements and values describe plants grown in Alva, Fla., with five plants per 16.5-cm containers in polyethylene-covered greenhouses, during the late spring under conditions which closely approximate commercial production. Night temperatures ranged between 13 to 24 degrees centigrade. Day temperatures ranged between 21 and 32 degrees centigrade. Plants were about 7 months old when descriptions were taken. In the description, color references are made to The Royal Horticultural Society Colour Chart except where general terms of ordinary dictionary significance are used.

Botanical classification: *Hibiscus rosa-sinensis* cultivar Whirl Wind.

Parentage:

*Female or seed parent.*—*Hibiscus rosa-sinensis* cultivar Waikiki, disclosed in U.S. Plant Pat. No. 7,834.

*Male or pollen parent.*—*Hibiscus rosa-sinensis* cultivar Florida Sunset, not patented.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, compact, uniform, dense and symmetrical plant habit.

*Branching habit.*—Freely branching, usually about four lateral branches develop after removal of terminal apex.

*Plant height, soil level to top of flowers.*—About 32 cm.

*Plant diameter, area of spread.*—About 42 cm.

*Lateral branch description.*—Length: About 22 cm. Diameter: About 5 mm. Texture; Immature, smooth; mature, woody and rough. Color: Immature: Green, 146A, overlaid with brown, close to 165A. Mature: Gray, close to 197A to 197B.

Foliage description:

*Arrangement.*—Alternate, single; numerous; symmetrical.

*Length.*—About 9.2 cm.

*Width.*—About 6.6 cm.

*Shape.*—Ovate.

*Apex.*—Acute.

*Base.*—Obtuse to slightly cordate.

*Margin.*—Crenate.

*Aspect.*—Undulate.

*Texture.*—Glabrous and glossy on both surfaces.

*Color.*—Young foliage, upper surface: Much greener than 147A. Young foliage, lower surface: Much greener than 147A. Mature foliage, upper surface: Darker and greener than 147A. Mature foliage, lower surface: Greener than 147A.

*Petiole.*—Length: About 3.3 cm. Diameter: About 2 mm. Texture: Mostly smooth with very fine pubescence on upper surface. Color: Close to 166A.

Flower description:

*Natural flowering season.*—Usually spring and summer or during periods of warm weather.

*Flower arrangement.*—Flowers arranged singly at terminal leaf axils. Very freely flowering with usually about three or four flower buds and/or open flowers per terminal apex. Flowers face upright to slightly outward.

*Flower appearance.*—Rounded, dark pink and light pink-edged bi-colored petals with dark red "eye". Flowers are open for about one day before closing. Flowers persistent.

*Flower diameter.*—About 11.75 cm.

*Flower bud* (*just before showing color*).—Rate of opening: About one or two days depending on temperatures. Length: About 3.2 cm. Diameter: About 1.6 cm. Shape: Elliptic.

*Petals.*—Texture: Smooth, satiny. Arrangement: Corolla consists of five petals that overlap. Shape: Spatulate with rounded apex. Margin: Entire, but slightly ruffled. Length: About 7.75 cm. Width: About 5 cm. Color: Upper surface: Center, 58B to 58C to darker than 52A; margin, a gradual color change of 54A to 54B to 54C to 56C to 56D over time. Lower surface: Center, 52D to 56D; margin, a gradual color change from 55D to 56A over time, slight yellow where petals overlap; base, 56D to white. Throat or "eye": Dark red, 53A; glossy.

*Sepals.*—Appearance: Five sepals fused into a star-shaped calyx. Shape: Linear. Texture: Slightly pubescent. Color, outer surface: 146A.

*Bracts.*—Appearance: About six fused at base. Length: About 1.6 cm. Width: About 3 mm. Shape: Linear. Color: 147A.

*Peduncles.*—Length: Short, about 4.2 cm. Diameter: About 2.5 mm at base. Angle: Upright to slightly bent. Strength: Strong, flexible. Texture: Slightly pubescent. Color: 144A; anthocyanin at knuckle and at base, close to 187A.

*Reproductive organs.*—Androecium: Stamen number: Numerous, about 47. Stamen length: About 5 mm. Filament color: White, 155D. Anther size: About 1 mm by 0.5 mm. Amount of pollen: Abundant. Pollen color: 14A. Gynoecium: Pistil length: About 8.5 cm. Style color: Base, 53A to 52A; mid-section and apex, white, 155D. Stigma appearance: Five, rounded. Stigma diameter: About 2 mm. Stigma color: Close to 17A.

Disease resistance: Resistance to known Hibiscus diseases has not been observed on plants grown under commercial greenhouse conditions.

Seed production: Seed production has not been observed.

It is claimed:

1. A new and distinct Hibiscus plant named 'Whirl Wind', as illustrated and described.

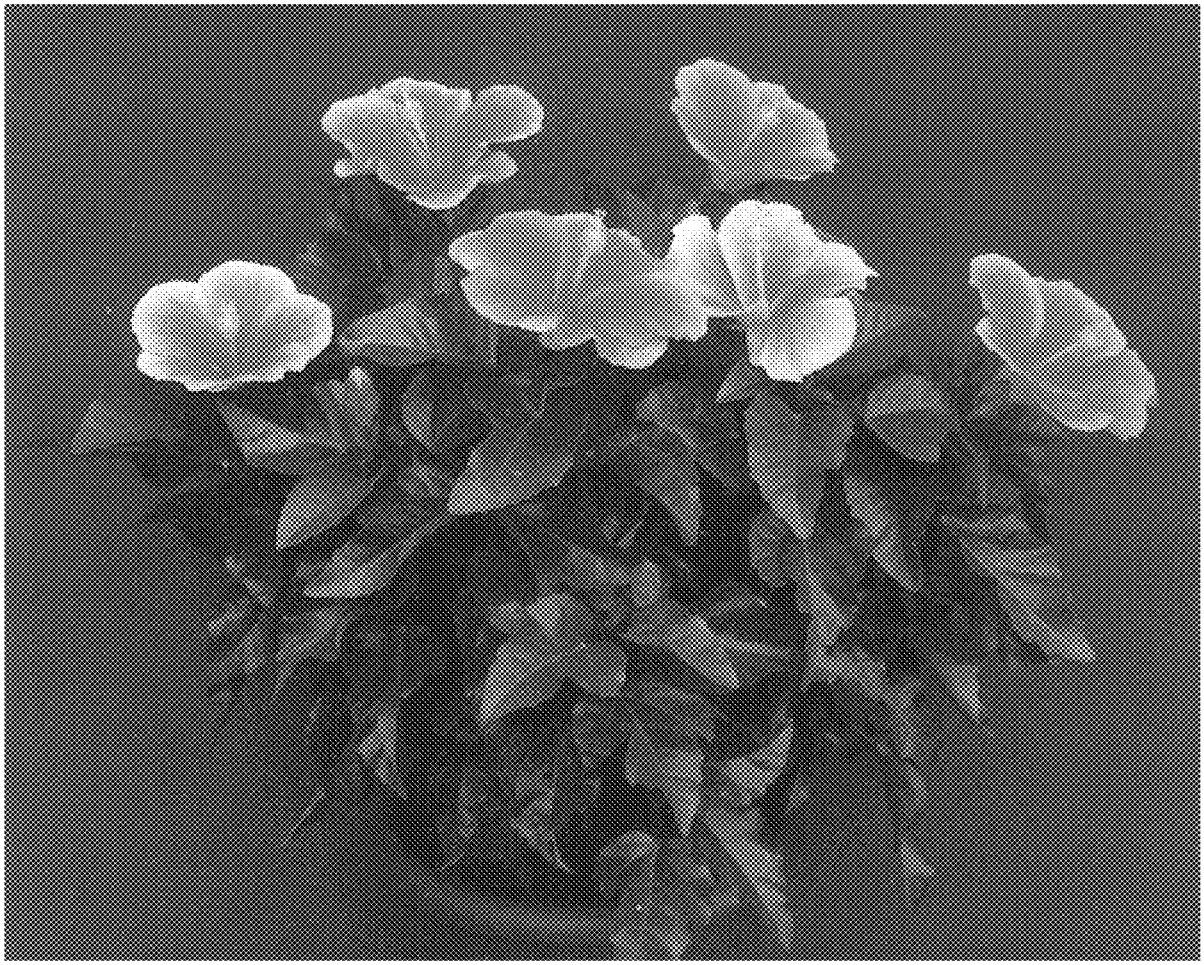

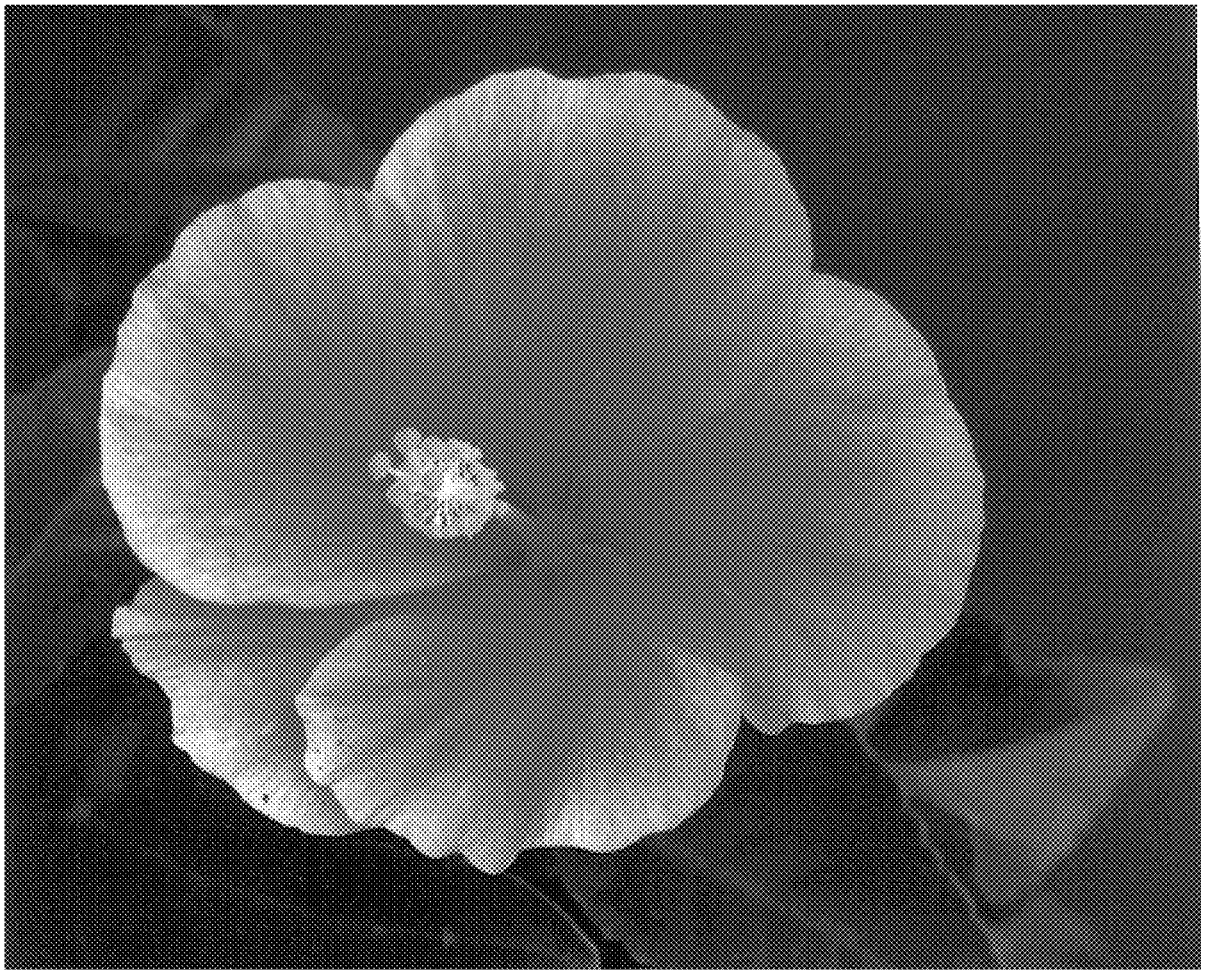

* * * * *